United States Patent [19]

Yasuda

[11] Patent Number: 5,606,071
[45] Date of Patent: Feb. 25, 1997

[54] PROCESS FOR PREPARING 5-ARYLHYDANTOINS USING 5-HYDANTOIN, A HALOGENATING AGENT AND P-PHENOL

[75] Inventor: Hiroshi Yasuda, Kanagawa, Japan

[73] Assignee: Showa Denko K.K., Tokyo, Japan

[21] Appl. No.: 321,833

[22] Filed: Oct. 6, 1994

[30] Foreign Application Priority Data

| Oct. 6, 1993 | [JP] | Japan | 5-250769 |
| Oct. 6, 1993 | [JP] | Japan | 5-250770 |
| Apr. 5, 1994 | [JP] | Japan | 6-067378 |

[51] Int. Cl.$^6$ ............ C07D 233/76; C07D 233/54; C07D 233/78; C07D 233/72; C07D 233/86
[52] U.S. Cl. ............ 548/321.1; 540/314; 548/317.1; 548/317.5; 548/319.1; 548/320.5; 562/451
[58] Field of Search ............ 548/317.5, 320.5, 548/321.1, 317.1, 319.1

[56] References Cited

U.S. PATENT DOCUMENTS

| 2,564,649 | 8/1951 | Rogers | 548/319.1 X |
| 2,626,263 | 1/1953 | Gaudry | 548/319.1 |
| 3,939,175 | 2/1976 | Schmidt et al. | 548/319.1 X |
| 4,044,019 | 8/1977 | Schmidt et al. | 548/319.1 X |
| 4,066,616 | 1/1978 | Lind | 548/319.1 X |
| 4,440,934 | 4/1984 | Kim et al. | 548/319.1 |
| 4,871,391 | 10/1989 | Wee et al. | 548/317.5 X |

FOREIGN PATENT DOCUMENTS

| 0353544 | 6/1975 | U.S.S.R. | 548/320.5 |

OTHER PUBLICATIONS

Ware, Elinor; The Chemistry of the Hydantoins, Nov. 3, 1949, pp. 403, 434, 435, 456, 461.

Henson, Edward B., et al.; Synthesis of D,L,β–Carboxyaspartic Acid From Hydantoin–5–Malonic Acid Diethyl Ester, Aug. 7, 1980, pp. 2561–2562.

Primary Examiner—Floyd D. Higel
Attorney, Agent, or Firm—Sughrue, Mion, Zinn, Macpeak & Seas

[57] ABSTRACT

The present invention provides a novel process for the preparation of 5-arylhydantoins as an important intermediate of (D)-arylglycines (e.g., (D)-p-hydroxyphenyl-glycine) useful for the synthesis of semisynthetic penicillines and cephalosporins, the process comprising (i) reacting a 5-unsubstituted hydantoin compound with a halogenating agent and (ii) reacting the resulting product with a p-unsubstituted phenol compound, the hydroxy group of which may be protected, to substitute the 5-position of the hydantoin compound with the phenol compound at the para position.

21 Claims, 3 Drawing Sheets

PROCESS FOR PREPARING 5-ARYLHYDANTOINS USING 5-HYDANTOIN, A HALOGENATING AGENT AND P-PHENOL

FIELD OF THE INVENTION

The present invention relates to a novel process for the preparation of 5-arylhydantoins as an important intermediate of (D)-arylglycines (e.g., (D)-p-hydroxyphenyl-glycine) useful for the synthesis of semisynthetic penicillines and cephalosporins.

BACKGROUND OF THE INVENTION

5-Arylhydantoins have been classically known to be synthesized in accordance with Bucherer-Berg method by which the corresponding arylaldehyde is reacted with ammonium carbonate and sodium cyanide (see "J. Prakt. Chem.", page 291, 140[1934]).

Many other synthesis methods have been known such as a method which comprises the reaction of glyoxylic acid, urea and an aryl compound under acidic conditions (see JP-A-54-106740 (the term "JP-A" as used herein means an "unexamined published Japanese patent application"), JP-B-55-22474 (the term "JP-B" as used herein means an "examined Japanese patent publication")), a method which comprises the reaction of 5-hydroxyhydaintoin with an aryl compound (see JP-A-54-138560), a method which comprises the reaction of allantoin with phenol (see JP-B-55-16582), a method which comprises the reaction of the reduction product of parabanic acid with phenol (see JP-A-3-206080) and a method which comprises the reaction of 4-hydroxyphenylketoacetal with phenol (see JP-A-4-364150).

Bucherer-Berg method requires the use of sodium cyanide, which is very dangerous. This method is also disadvantageous in that the resulting crude hydantoin contains a large amount of products of the secondary reaction occurring with the oxidation of phenol ring under alkaline conditions and thus is liable to coloration.

The synthesis methods which comprise the use of starting materials such as glyoxylic acid, 5-hydroxy-hydantoin, allantoin, parabanic acid and 4-hydroxyphenylketo-acetal leave something to be desired because these starting materials are expensive.

SUMMARY OF THE INVENTION

It is therefore an object of the present invention to provide a process for the preparation of 5-arylhydantoins with a high purity in a high yield.

It is another object of the present invention to provide a process for the preparation of industrially advantageous 5-arylhydantoins wherein all the reactions can be effected in the same solvent system in the same reaction vessel.

It is a further object of the present invention to provide starting materials useful for the preparation of 5-arylhydantoins.

These and other objects of the present invention will become more apparent from the following detailed description and examples.

The inventors have made extensive studies to eliminate these difficulties. As a result, a novel process for the synthesis of 5-arylhydantoins from cheap hydantoin compounds as starting materials has been found. Thus, the objectives of the present invention have been achieved.

The present invention provides a process for the preparation of 5-arylhydantoins, which comprises (i) reacting a 5-unsubstituted hydantoin compound and a halogenating agent, and (ii) reacting the resulting product and a p-unsubstituted phenol compound, the hydroxy group of which may be protected, to thereby substitute the 5-position of the hydantoin compound with the phenol compound at its p-position.

BRIEF DESCRIPTION OF THE DRAWINGS

By way of example and to make the description more clear, reference is made to the accompanying drawings in which.

DETAILED DESCRIPTION OF THE INVENTION

Figure 1:
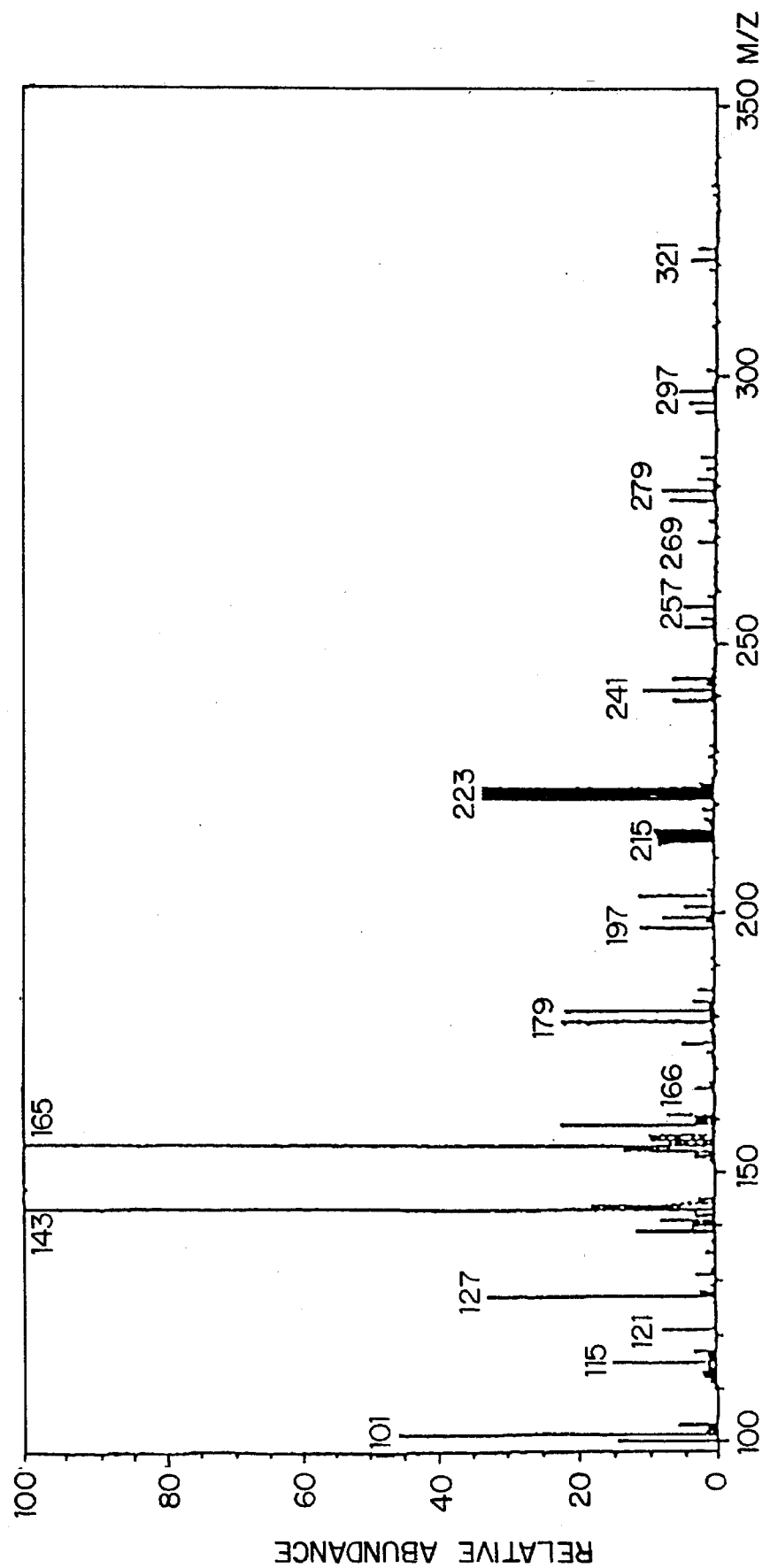
FIG. 1 shows the mass analysis spectrum (CI-MS) of a novel 5-bromohydantoin compound as a starting material useful for the preparation of 5-arylhydantoins of the present invention.

The 5-unsubstituted hydantoin compound which can be used in the present invention is preferably represented by formula (I)

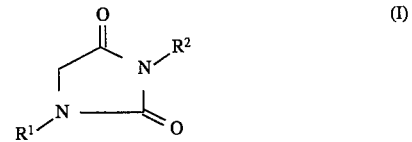

wherein $R^1$ represents a hydrogen atom or a protective group for the nitrogen atom, and $R^2$ represents an alkyl group having 1 to 8 carbon atoms (e.g., methyl, ethyl, octyl), an alkenyl group having 3 to 10 carbon atoms (e.g., allyl), an alkynyl group having 3 to 10 carbon atoms (e.g., propargyl), an acyl group having 2 to 10 carbon atoms (e.g., acetyl, propionyl, benzoyl), an aryl group preferably having 6 to 10 carbon atoms which may be substituted (e.g., phenyl, tolyl), an aralkyl group preferably having 7 to 16 carbon atoms which may have a substituent on the aryl moiety (e.g., benzyl, p-methoxybenzyl), an aminocarbonyl group preferably having 1 to 10 carbon atoms which may have a substituent on the amino moiety (e.g., N-methylaminocarbonyl), an alkoxycarbonyl group having 3 to 8 carbon atoms (e.g., methoxycarbony, ethoxycarbonyl), an aryloxycarbonyl group preferably having 7 to 10 carbon atoms which may have a substituent on the aryl moiety (e.g., phenoxycarbonyl), an aralkyloxycarbonyl group preferably having 8 to 17 carbon atoms which may have a substituent on the aryl moiety (e.g., benzyloxycarbonyl), a nitrogen substituent group (e.g., azo), a sulfinyl group having 1 to 8 carbon atoms, and a sulfonyl group having 1 to 8 carbon atoms.

The protective group for $R^1$ in formula (I) is a group satisfying the following requirements: (i) does not change during an objective reaction (a halogenation reaction in this case); (ii) does not hinder the objective reaction; and (iii) is released from the protecting portion without any changes at the other portions after the objective reaction. In other words, the protective group for $R^1$ is a group which does not hinder the halogenation reaction and the subsequent reaction with the phenol compound and which is released under certain conditions to provide a nitrogen-hydrogen bond after these reactions. Reference may be made to Theodora W. Greene and Peter G. M. Wats, *Protective Groups in Organic Synthesis, Second Edition*, published by John Wiley & Sons, Inc.

Preferred examples of the protective group for $R^1$ include a methyl group, an alkenyl group having 3 to 10 carbon atoms (e.g., allyl), an alkynyl group having 3 to 10 carbon atoms (e.g., propargyl), an acyl group having 2 to 10 carbon atoms (e.g., acetyl, propionyl, benzoyl), an aralkyl group preferably having 7 to 10 carbon atoms which may have a substituent on the aryl moiety (e.g., benzyl, p-methoxybenzyl), an aminocarbonyl group preferably having 1 to 10 carbon atoms which may have a substituent on the amino moiety (e.g., N-methylaminocarbonyl), an alkoxycarbonyl group having 3 to 8 carbon atoms (e.g., methoxycarbonyl, ethoxycarbonyl), an aryloxycarbonyl group preferably having 7 to 10 carbon atoms which may have a substituent on the aryl moiety (e.g., phenoxycarbonyl), and an aralkyloxycarbonyl group preferbly having 8 to 17 carbon atoms which may have a substituent on the aryl moiety (e.g., benzyloxy carbonyl).

Of the 5-unsubstituted hydantoin compounds, preferred are hydantoin, 3-methylhydantoin, 1-benzylhydantoin, 1-acetylhydantoin, and 1-benzyl-3-methylhydantoin, but the present invention is not limited thereto.

The halogenating agent to be used in the present invention is an organic or inorganic reagent by which a halogen atom can be introduced into the reaction substrate (5-unsubstitued hydantoin compound). Examples of the organic or inorganic reagent employable in the present invention include halogen atoms such as chlorine, bromine and iodine, mixed halogens such as bromine chloride (BrCl) and iodine bromide (IBr), haloimides or haloamides such as N-chlorosuccinimide and N-bromoacetamide, perhalogenates such as calcium hypochlorite $(Ca(ClO)_2)$, calcium hypobromite $(Ca(BrO)_2)$, t-butylhypochlorite and t-buthylhypobromite, perhalogenic esters, and chlorides and bromides such as sulfuryl chloride and sulfuryl bromide. The halogenating agent employable in the present invention is not limited to the foregoing halogenating agents. Halogenating agents commonly used in organic synthesis can be used.

The amount of the halogenating agent to be used in the reaction with the 5-unsubstituted hydantoin compound is preferably 1 molar equivalent based on 1 molar equivalent of the hydantoin compound. The reaction temperature is between about 20° C. and 100° C., preferably between 40° C. and 80° C. The reaction time is preferably between 0.5 and 8 hours.

The solvent to be used in the halogenation reaction may be any solvent in which even traces of the 5-unsubstituted hydantoin compound and halogenating agent and the p-unsubstituted phenyl compound of formula (III) added later can be solved. In the present reaction, acetic acid or dioxane, which exerts a remarkable solvent effect, is preferably used. As the reaction solvent there may be preferably used a solvent system substantially free of water. Solvents which can be used in the present invention will be exemplified below, but the present invention should not be construed as being limited thereto.

Ether series: dioxane, tetrahydrofuran, dimethoxyethane, diglyme, triglyme, etc.

Alcohol series: ethanol, methanol, isopropanol, butanol, etc.

Carboxylic acid series: acetic acid, propionic acid, etc.

Nitrile series: acetonitrile, propionitrile, butylonitril, adiponitrile, etc.

Halogen series: chloroform, dichloroethane, etc.

Aprotic polar solvent: dimethylformamide, dimethyl sulfoxide, etc.

The reaction of hydantoin with the halogenating agent can efficiently proceed in the presence of an acid or radical reaction initiator. As such an acid there may be used an inorganic acid such as hydrochloric acid, hydrobromic acid, hydroiodic acid and sulfuric acid; an organic acid such as acetic acid, propionic acid, oxalic acid, succinic acid, adipic acid, trifluoroacetic acid, p-toluenesulfonic acid, benzenesulfonic acid, methanesulfonic acid and trifluoromethanesulfonic acid; a Lewis acid such as titanium tetrachloride, zirconium tetrachloride, vanadium trichloride, iron trichloride, iron tribromide, aluminum chloride, aluminum bromide, boron trifluoride ether complex, boron trichloride, boron tribromide, tellurium tetrachloride, antimony trichloride, antimony pentachloride, silica tetrachloride, bismuth trichloride, bismuth tribromide, zinc chloride, zinc bromide, zinc trifluoromethanesulfonate, stannous chloride, stannic chloride, and stannous trifluoromethanesulfonate; and a solid acid such as silica gel, acidic alumina, acid clay and zeolite. Examples of the radical reaction initiator include dialkyl peroxides such as di-t-butyl peroxide, diacyl peroxides such as dibenzyl peroxide, peresters such as di-t-butyl peroxalate, and azo compounds such as azobisisobutylonitrile and phenylazatriphenylmethane.

With the progress of the halogenation reaction, hydrogen halide derived from halogen is released, accelerating the reaction. Accordingly, the amount of the acid or radical reaction initiator to be added may be extremely small. For example, the inorganic or organic acid and the Lewis acid or solid acid may be added in an amount of from 1/1000 to 1/200 mol equivalent and from 1/500 to 1/100 mol equivalent, respectively, per mol equivalent of the 5-unsubstituted hydantoin compound. The radical reaction initiator may be added in an amount of from 1/1000 to 1/200 mol equivalent per mol equivalent of the 5-unsubstituted hydantoin compound.

Figure 2:
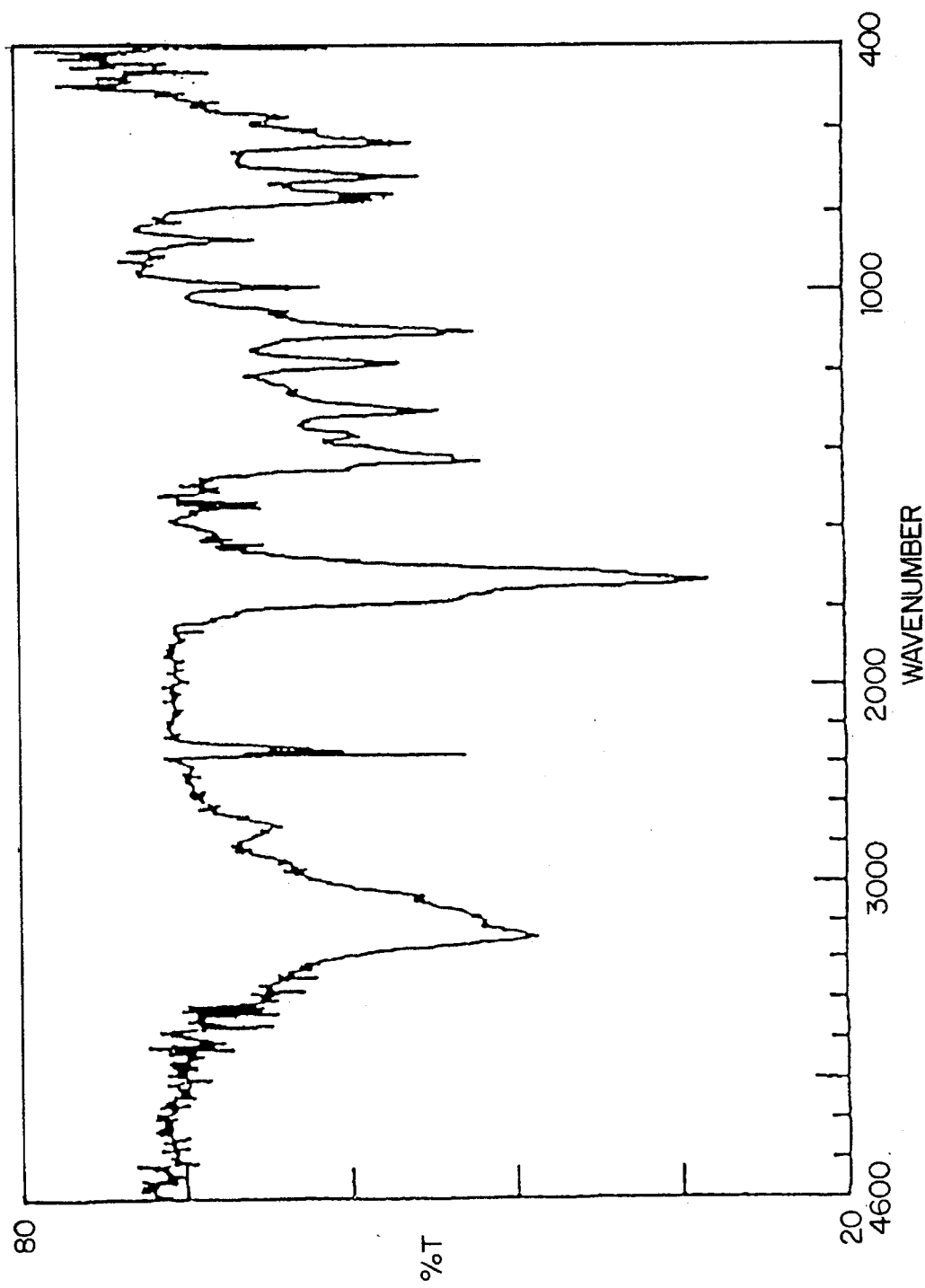
FIG. 2 shows the infrared absorption spectrum (FTIR reflection method with KBr powder) of 5-bromohydantoin.
Figure 3:
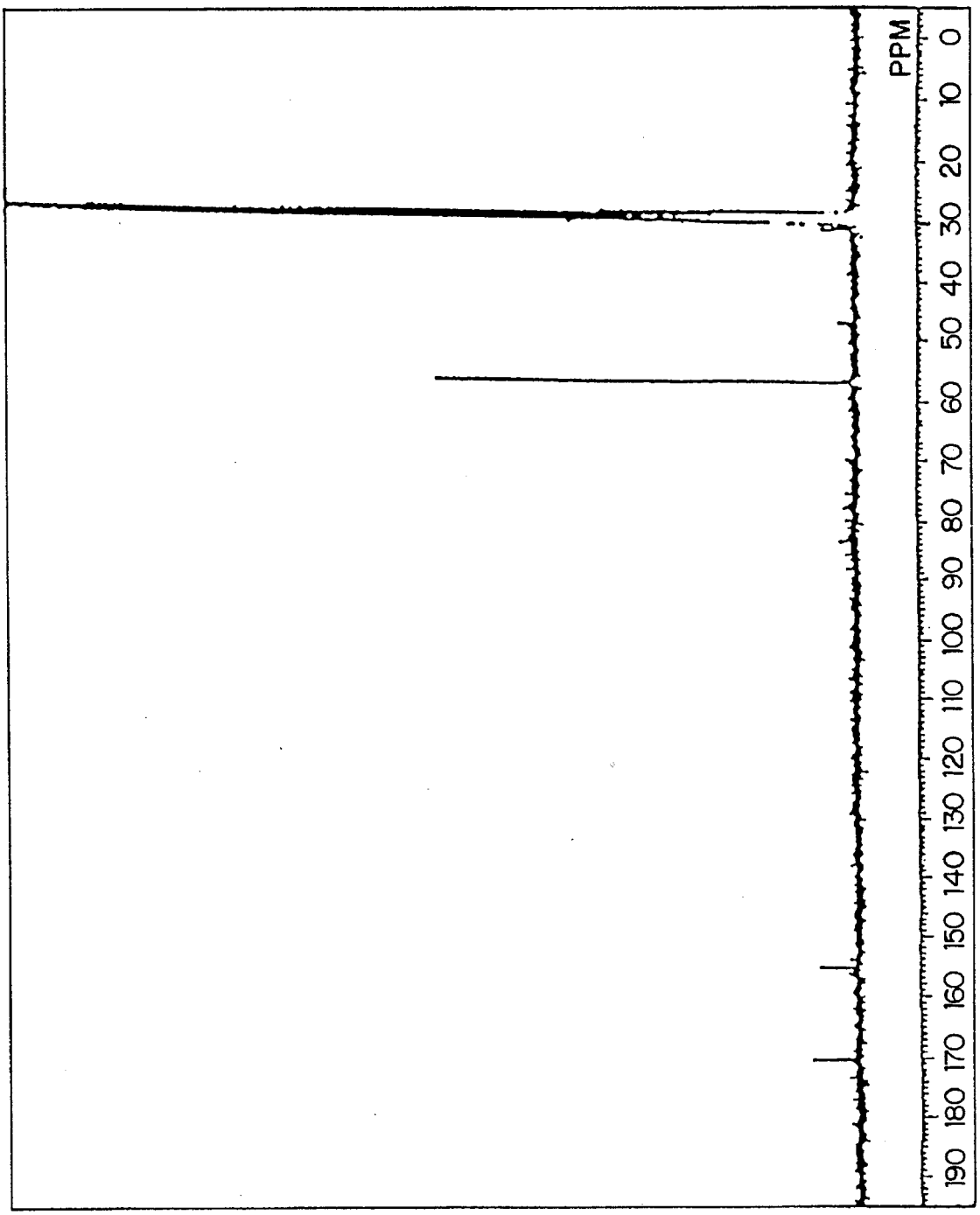
FIG. 3 shows $^{13}$C-NMR spectrum (determined in heavy acetone at 400 MHz) of 5-bromohydantoin.

5-Bromohydantoin obtained by halogenation of hydantoin with the foregoing brominating agent as a halogenating agent is a novel compound having the following properties:
(1) White solid
(2) Mass analysis [CI-MS] (as set forth in FIG. 1) m/z 179 (M+H)+, 181 ((M+2)+H)
(3) Molecular formula: $C_3H_3BrN_2O_2$
(4) Infrared absorption spectrum FTIR reflective method with KBr powder (as set forth in FIG. 2)
(5) $^{13}$C-NMR (as set forth in FIG. 3)

Determined in heavy acetone at 400 MHz and room temperature
(6) Solubility: soluble in dioxane, chloroform, acetic acid and acetone; difficultly soluble in hexane and toluene.

5-Bromohydantoin according to the present invention has the following chemical structure (II):

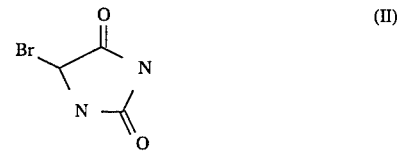

The chemical structure of 5-bromohydantoin was determined by studying in detail the mass analysis spectrum, infrared absorption spectrum and $_{13}$C nuclear magnetic resonance spectrum thereof.

The reaction product obtained by the halogenation of the 5-unsubstituted hydantoin compound is unstable so that it is difficult to isolate the product and to define its chemical structure. From the experimental facts as described below, however, it is presumed that the reaction product has a chemical structure represented by formula (II')

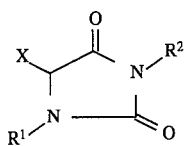

(II')

wherein $R^1$ and $R^2$ have the same meanings as defined above, and X represents a chlorine atom, a bromine atom or an iodine atom. The experimental facts are that (i) 5-hydroxyhydantoin is produced in high yield when water is reacted with a reaction product of 1 mol of hydantoin and 1 mol of bromine in dioxane (solvent), (ii) allantoin is produced in high yield when urea is reacted with the reaction product, (iii) 5-(p-hydroxyphenyl)hydantoin is produced in high yield when phenol is reacted with the reaction product. Besides, it has been known that bromine is introduced at 5-position of hydantoin ring upon bromination of 5-phenylhydantoin, (which is not the hydantoin compound of formula (I) though) in acetic acid (solvent) (see *Chem. Rev.*, p. 403 (1949)). These facts provide reasonable basis for the above presumption.

Since the reaction product obtained by the halogenation of the 5-unsubstituted hydantoin compound is unstable, it is preferably reacted with the p-unsubstituted phenol compound without being isolated from the synthesis product. In some detail, the phenol compound is preferably added to the reaction system after the completion of the reaction of the hydantoin compound with the halogenating agent. The phenyl compound may be added in the presence of the halogenating agent. However, halides of the phenol compound are by-produced, lowering the yield of the 5-aryl hydantoin compound per the phenol compound. The halogenating agent, if it is volatile, can be removed by introducing gas such as nitrogen into the reaction system. If it is nonvolatile, the halogenating agent may be decomposed away by a proper reducing agent.

The p-unsubstituted phenol compound which can be used in the present invention is preferably represented by formula (III)

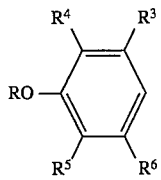

(III)

wherein R represents a hydrogen atom or a protective group for a phenolic hydroxyl group, and $R^3$, $R^4$, $R^5$ and $R^6$ each represent a hydrogen atom, or a group that does not substantially impair the para-orientation property of the phenol compound.

The protective group for R in formula (III) is a group satisfying the same requirements as described for $R^1$ (but in the case, the objective reaction is the reaction with the 5-halohydantoin of formula (II')), and which is released under certain conditions to provide an oxygen-hydrogen bond.

Preferred examples of the protective group for R include an alkyl group having 1 to 8 carbon atoms (e.g., methyl, ethyl, octyl), an alkenyl group having 3 to 10 carbon atoms (e.g., allyl), an alkynyl group having 3 to 10 carbon atoms (e.g., propargyl), an acyl group having 2 to 10 carbon atoms (e.g., acetyl, propionyl, benzoyl), an aralkyl group preferably having 7 to 16 carbon atoms which may have an substituent on an aryl moiety (e.g., benzyl, p-methoxybenzyl), an aminocarbonyl group preferably having 1 to 10 carbon atoms which may have an substituent on the amino moiety.(e.g., N-methylaminocarbonyl), an alkoxycarbonyl group having 3 to 8 carbon atoms (e.g., methoxycarbonyl, ethoxy-carbonyl), an aryloxycarbonyl group preferably having 7 to 10 carbon atoms which may have an substituent on the aryl moiety (e.g., phenoxycarbonyl), an aralkyloxycarbonyl group preferably having 8 to 17 carbon atoms which may have an substituent on the ary moiety (e.g., benzyloxycarbonyl), a trialkylsilyl group having the alkyl moiety of 1 to 4 carbon atoms (e.g., trimethylsilyl, triethylsilyl, t-butyldimethyl-silyl), dialkylarylsilyl group which may have an substituent on the aryl moiety and which has the alkyl moiety of 1 to 4 carbon atoms (e.g., dimethylphenylsilyl), alkyldiarylsilyl group which may have an substituent on the aryl moiety and which has the alkyl moiety of 1 to 4 carbon atoms (e.g., methyldiphenylsilyl), triarylsilyl group which may have an substituent on the aryl moiety (e.g., triphenylsilyl), and phosphate ester derivatives (e.g., those represented by formula (IV), (V) or (VI))

(IV)

(V)

(VI)

The groups for $R^3$, $R^4$, $R^5$ and $R^6$ are not particularly limited as long as they do not substantially impair the para-orientation property of the phenol compound. Examples of the group include a halogen atom (e.g., F, Cl, Br, I), a hydroxy group, an alkyl group having 1 to 4 carbon atoms (e.g., methyl, ethyl), an alkoxy group having 1 to 4 carbon atoms (e.g., methoxy, ethoxy), an alkoxy carbonyl group having 1 to 4 carbon atoms (e.g., methoxycarbonyl, ethoxycarbonyl), an amino group which may be substituted (e.g., dimethylamino), an aminocarbonyl group preferably having 1 to 10 carbon atoms which may have a substitutent on the amino moiety (e.g., methylaminocarbonyl), a nitoro group, a nitroso group, a thiol group, and a sulfide group having 1 to 4 carbon atoms (e.g., methylsulfide).

Of the p-unsubstituted phenol compound of the present invention, preferred are phenol, catechol, resorcinol, anisole, o-cresol, m-cresol, o-methoxyphenol, m-methoxy-phenol, o-chlorophenol, m-chlorophenol, o-anisidine, m-amisidine, 2,5-dimethylphenol and 2,5-di-t-butylphenol. However, the present invention should not be construed as being limited thereto.

The reaction of the compound of formula (II') and the p-unsubstituted phenol compound of formula (III) produces a 5-arylhydantoin as represented by formula (IV)

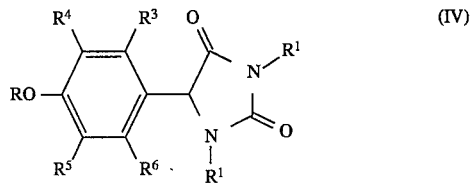

(IV)

wherein R, $R^1$, $R^2$, $R^3$, $R^4$, $R^5$ and $R^6$ have the same meanings as defined above.

The mechanism of the reaction of the 5-halohydantoin compound represented by formula (II') with the phenol compound represented by formula (III) is unknown. This reaction is possibly of Friedel-Crafts type. This is substantiated by the following facts characteristic to Friedel-Crafts reaction (1) A carbon-carbon bond formation reaction of haloalkane with aryl compound occurs;

(2) The 5-halohydantoin compound (II') can be easily substituted for hydrogen atom in p-position to OR of the phenol compound, which position is particularly activated by the substituent OR in the phenol compound (III);

(3) The rate of production of 5-arylhydantoins (IV) is proportional to the product of (II') and (III), that is, represented by an equation of the second order.

Although Friedel-Crafts reaction of a haloalkane with an aromatic compound generally requires the presence of a Lewis acid, the reaction according to the present invention is specific in that it proceeds even in the absence of such an acid catalyst. The reaction of the present invention in the absence of Lewis acid is economical and advantageous because the production cost of 5-aryl hydantoins can be lowered and corrosion of the reactor and complexity in separation of the Lewis acid and the product can be avoided.

The amount of the phenol compound (III) to be used is preferably at least 1 molar equivalent, more preferably 1.5 to 3 molar equivalents based on 1 molar equivalent of the 5-halohydantoin compound (II'). The reaction temperature is between about $-10°$ C. and $120°$ C., preferably between $0°$ C. and $110°$ C., more preferably between $40°$ C. and $60°$ C. If the reaction temperature is too low, the time required until the completion of the reaction is remarkably long. On the contrary, if the reaction temperature is too high, the reaction substrate is decomposed, lowering the yield of 5-arylhydantoin (IV). The reaction time is preferably between 2 hours and 10 hours, more preferably between 3 hours and 8 hours. The reaction time depends on the amount of the phenol compound (III) added and the reaction temperature. When the phenol compound (III) is added in an amount of twice or three times that of 5-halohydantoin (II') charged, and the reaction thereof is effected at a temperature of $0°$ C. to $50°$ C., the reaction is almost completed in 2 to 12 hours.

The reaction of the compound (II') obtained by the reaction of the 5-unsubstituted hydantoin compound of formula (I) with the halogenating agent, with the phenol compound (III) may be effected in the same reaction solvent as that used in the reaction of the hydantoin compound of formula (I) with the halogenating agent, optionally mixed with other solvents. Alternatively, the reaction solvent used in the reaction of the hydantoin compound of formula (I) with the halogenating agent may be replaced by another solvent upon the subsequent reaction. It is extremely efficient in the control of reaction to use the same solvent system for the two successive reactions.

In the reaction for producing arylhydantoins, decomposed substances are not generally by-produced and the resulting arylhydantoins are not colored, while the starting materials (i.e., a hydantoin compound, a halogenating agent and a phenol compound) influence the results to some extent. By-products in the reaction are 5-(o-substituted aryl) hydantoins resulted by the reaction of the ortho position of the phenol compound and the 5-position of the hydantoin compound. For example, when hydantoin is reacted with a halogenating agent and the resulting product is then reacted with phenol, 5-(p-hydroxyphenyl)hydantoin is obtained as a main product, with by-produced 5-(o-hydroxyphenyl)hydantoin. The production ratio of the objective p-substituted product to the by-produced o-substituted product is generally within the range of 2/1 to 8/1, while it may vary depending on the reaction conditions and the reactants. Further, the p-substituted product has generally a higher crystallinity than that of the o-substituted product (though this tendency varies depending on the kind of arylhydantoins), so that the objective p-substituted product can be separated by recrystallization of the products or by utilizing the difference in solubility of the products. For example, when the reaction for producing 5-(hydroxyphenyl) hydantoins is conducted using an optimum solvent, its p-substituted product (5-(p-hydroxyphenyl)-hydantoin) can be isolated alone as a precipitate.

The 5-arylhydantoin obtained according to the present invention can be converted to an arylglycine which is mainly useful as an intermediate of medicines. A typical example of arylglycine is (D)-p-hydroxyphenylglycine, which is an important intermediate of a semisynthetic penicillin such as amoxicillin.

The synthesis of a penicillin compound from the 5-arylhydantoin can be accomplished by a process which comprises the steps of (1) deprotection of the phenolic hydoxyl group in the 5-arylhydantoin and the-protective group at the 1-position of hydantoin; (2) optical resolution to an arylglycine; (3) synthesis of an alkaline metal salt of N-(1-alkoxycarbonylpropene-2-il)-(D)-α-amino-phenylacetic acid (commonly referred to as "dane salt") from the arylglycine; and (6) condensation reaction of 6-aminopenicillanic acid with the dane salt.

Among the foregoing steps, the order of the step (1) (deprotection) and the step (2) (optical resolution) differs with how to effect the optical resolution of the arylglycine.

The foregoing steps will be further described with reference to the synthesis of amoxicillin.

Firstly, (D)-p-hydroxyphenylglycine is synthesized by the asymmetric hydrolysis of a 5-arylhydantoin by micro-organisms or the optical resolution of a 5-arylhydantoin.

In the case of asymmetric hydrolysis by micro-organisms, there is used 5-(p-hydroxyphenyl)hydantoin as the 5-arylhydantoin. 5-(p-hydroxyphenyl)hydantoin is subjected to asymmetric hydrolysis in the presence of an enzyme such as hydantoinase. Thus, (D)-p-hydroxyphenyl-N-carbamoyl-glycine is quantitatively derived from 5-(p-hydroxyphenyl) hydantoin with the occurrence of asymmetric conversion [*J. Ferment. Technol.*, 57, page 328, (1979)]. The N-carbamoyl group is then decomposed by nitric acid to obtain (D)-p-hydroxyphenyl-glycine.

In the case of optical resolution, a 5-arylhydantoin in which the phenolic hydroxyl group may be protected is converted to arylglycine esters in which the carboxyl group is properly protected and aryl-N-acyl-glycines in which the amino group is protected by proper protective groups, respectively. The arylglycine esters are then acted on by an acid to undergo optical resolution (JP-A-49-66651). On the other hand, the aryl-N-acyl-glycines are then acted on by a base to undergo optical resolution (JP-A-50-52041). Alternatively, the 5-arylhydantoin may be directly subjected to optical resolution with a resolving agent such as p-toluenesulfonic acid without protecting the carboxyl group and amino group (JP-A-50-111033). After optical resolution, the protective group is then deprotected such that no racemization occurs to obtain (D)-p-hydroxyphenylglycine.

In the synthesis of antibiotics, (D)-p-hydroxyphenyl-glycine is converted to an alkaline metal salt of N-(1-alkoxycarbonylpropene-2-il)-(D)-α-amino(p-hydroxyphenyl)-acetic acid (III) called "dane salt" obtained by the condensation of an alkaline metal salt of the carboxylic group in (D)-p-hydroxyphenylglycine with acetoacetic esters (JP-A-2-49757). As the alkaline metal there is used sodium, potassium or the like. As the acetoacetic esters there are used acetoacetic methyl ester, acetoacetic ethyl ester, etc.

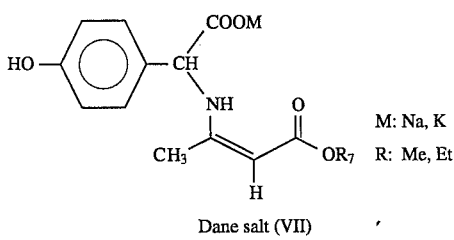

Dane salt (VII)    M: Na, K    R: Me, Et

The dane salt is then converted to an anhydrous mixed acid so that it is activated. It is then condensed with the amino group at the 6-position of 6-amino-2,2-dimethylpenam-3-carboxylic compound (commonly referred to as "6-amino-penicillanic acid). After condensation, the acetoacetic ester is deprotected by a weak acid to obtain a penicillin antibiotic [*J. Chem. Soc.* (C) page 1920 (1971)].

In the synthesis of amoxicillin, sodium N-(1-methoxycarbonylpropene-2-il)-(D)-α-amino-(p-hydroxyphenyl)acetate is used as a dane salt. The dane salt is reacted with an ester activating agent such as ethyl chlorocarbonate to obtain an anhydrous mixed acid. The anhydrous mixed acid is then allowed to undergo condensation reaction with 6-aminopenicillanic acid to form an amide. The methyl acetoacetate is then removed with a dilute hydrochloric acid to obtain amoxicillin (VIII).

Amoxicillin (VIII)

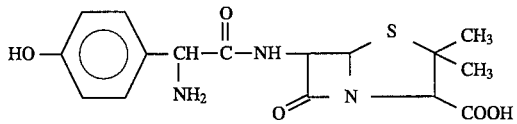

The present invention will be further described in the following examples, but the present invention should not be construed as being limited thereto.

EXAMPLE 1

4.0 g (40 mmol) of hydantoin, 10 ml of dioxane, and 2.0 ml (40 mmol) of bromine were mixed at room temperature. The reaction mixture was then vigorously stirred at a temperature of 100° C. for 30 minutes. The reaction mixture was then cooled to a temperature of 0° C. To the reaction mixture was then added 5.7 g (60 mmol) of phenol. The reaction mixture was then allowed to undergo reaction at a temperature of 0° C. for 12 hours. The resulting precipitate was recovered by filtration, washed with water, and then dried to obtain 5.53 g (yield: 72%) of 5-(p-hydroxy-phenyl)hydantoin. The crystal thus obtained exhibited a melting point of 263° to 265° C. The infrared spectrum, NMR spectrum and Rf value of silica gel thin layer chromatography of the crystal showed a complete conformance to that of a specimen synthesized by the method as disclosed in JP-B-55-22474.

EXAMPLE 2

4.0 g (40 mmol) of hydantoin, 50 ml of dioxane, 5.4 g (40 mmol) of sulfuryl chloride, and 0.01 g of azobisiso-butylonitrile were mixed. The reaction mixture was then stirred at a temperature of 90° C. for 5 hours. The reaction system was then allowed to cool to room temperature. To the reaction system was then added 7.6 g (80 mmol) of phenol. The reaction mixture was then allowed to undergo reaction at a temperature of 80° C. for 5 hours. The resulting precipitate was recovered by filtration, washed with water, recrystallized from water and then dried to obtain 0.41 g (yield: 5.3%) of 5-(p-hydroxyphenyl)hydantoin.

EXAMPLE 3

4.0 g (40 mmol) of hydantoin, 30 ml of acetic acid, and 2.0 ml (40 mmol) of bromine were mixed at room temperature. The reaction mixture was then vigorously stirred at a temperature of 40° C. for 2 hours. The reaction system was then allowed to cool to room temperature. To the reaction system was then added 5.7 g (60 mmol) of phenol. The reaction mixture was then allowed to undergo reaction at a temperature of 100° C. for 6 hours. The resulting precipitate was recovered by filtration, washed with water, and then dried to obtain 4.0 g (yield: 52%) of 5-(p-hydroxyphenyl) hydantoin.

EXAMPLE 4

4.0 g (40 mmol) of hydantoin, 50 ml of dioxane, 0.025 g of zinc bromide, and 2.0 ml (40 mmol) of bromine were mixed at room temperature. The reaction mixture was then vigorously stirred at a temperature of 60° C. for 30 minutes. The reaction system was then allowed to cool to room temperature. To the reaction system was then added 7.6 g (80 mmol) of phenol. The reaction mixture was then allowed to undergo reaction at a temperature of 50° C. for 4 hours. The resulting precipitate was recovered by filtration, washed with water, and then dried to obtain 4.69 g (yield: 61%) of 5-(p-hydroxyphenyl)hydantoin.

EXAMPLE 5

A mixture of 4.00 g (40 mmol) of hydantoin, 6.4 g (40 mmol) of bromine, 0.01 g of methanesulfonic acid, and 30 ml of dioxane was heated to a temperature of 100° C. with stirring for 3 minutes. The reaction mixture was further stirred at a temperature of 50° C. until bromine disappeared. To the reaction mixture was then added 7.52 g (80 mmol) of phenol. The reaction mixture was then heated to a temperature of 50° C. with stirring for 4 hours. The reaction mixture was then allowed to cool to room temperature. The reaction mixture was further cooled over an ice bath for 2 hours. The resulting crystal was recovered by filtration, washed thoroughly with water, and then air-dried to obtain 4.69 g (24.4 mmol; yield: 61%) of 5-(p-hydroxyphenyl)-hydantoin in the form of white crystal.

EXAMPLE 6

2.00 g (20 mmol) of hydantoin was dissolved in 30 ml of acetic acid. The solution was then heated to a temperature of 80° C. under stirring with chlorine being introduced thereinto for 5 hours. The reaction system was then allowed to cool to room temperature. The dissolved chlorine was then removed by introducing nitrogen into the reaction system. To the reaction solution was then added 3.76 g (40 mmol) of phenol. The reaction mixture was then heated to a temperature of 70° C. for 8 hours. The reaction solution was then allowed to cool to room temperature. The reaction solution was then concentrated under reduced pressure to distill off acetic acid and phenol. To the resulting residue was then added 50 ml of water. The mixture was then heated to effect dissolution. The solution was then allowed to stand. The resulting precipitate was recovered by filtration, washed with water, and then dried to obtain 0.55 g (2.89 mmol;

yield: 28.9%) of 5-(p-hydroxyphenyl)hydantoin in the form of white flake crystal.

EXAMPLE 7

1.34 g (10 mmol) of 5-chlorohydantoin and 1.88 g (20 mmol) of phenol were dissolved in 10 ml of dioxane. The solution was then heated to a temperature of 70° C. with stirring for 6 hours. The reaction system was then allowed to cool to room temperature. The reaction system was further cooled over an ice bath for 2 hours. The resulting crystal was recovered by filtration, washed thoroughly with water, and then air-dried to obtain 0.93 g (4.8 mmol; yield: 48%) of 5-(p-hydroxyphenyl)hydantoin in the form of white crystal. The crystal thus obtained exhibited a melting point of 262° to 264°0 C. (decomposition). The IR spectrum, NMR spectrum, and Rf value of thin layer chromatography showed a good conformance to that of a specimen which had been separately synthesized.

EXAMPLE 8

Synthesis of 5-bromohydantoin)

10.0 g (100 mmol) of hydantoin, 100 ml of dioxane, 5.0 ml (100 mmol) of bromine, and 0.01 g of boron trifluoride ether complex were mixed at room temperature. The mixture was then stirred with vigorous stirring at a temperature of 60° C. for 30 minutes. The reaction solution was then allowed to cool to room temperature. The solvent was then distilled off. The residue was then dried under reduced pressure to quantitatively obtain 5-bromohydantoin.

EXAMPLE 9

4.0 g (40 mmol) of hydantoin, 30 ml of acetic acid, and 2.0 ml (40 mmol) of bromine were mixed at room temperature. The mixture was then vigorously stirred at a temperature of 40° C. for 2 hours. The reaction solution was then allowed to cool to room temperature. The solvent was then distilled off. The residue was then dried under reduced pressure to obtain 7.0 g (yield: 98%) of 5-bromohydantoin.

EXAMPLE 10

4.56 g (40 mmol) of 3-methyl-hydantoin, 30 ml of acetic acid, and 2.0 ml (40 mmol) of bromine were mixed at room temperature. The reaction mixture was then vigorously stirred at a temperature of 40° C. for 2 hours. The reaction mixture was then allowed to cool to room temperature. To the reaction mixture was then added 5.7 g (60 mmol) of phenol. The reaction mixture was then allowed to undergo reaction at a temperature of 100° C. for 6 hours. The resulting precipitate was recovered by filtration, washed with water, and then dried to obtain 4.20 g (yield: 51%) of 5-(p-hydroxyphenyl)-3-methyl-hydantoin.

EXAMPLE 11

4.56 g (40 mmol) of 3-methyl-hydantoin, 30 ml of acetic acid, and 2.0 ml (40 mmol) of bromine were mixed at room temperature. The reaction mixture was then vigorously stirred at a temperature of 40° C. for 2 hours. The reaction mixture was then allowed to cool to room temperature. To the reaction mixture was then added 60 mmol of anisole. The reaction mixture was then allowed to undergo reaction at a temperature of 100° C. for 6 hours. The resulting precipitate was recovered by filtration, washed with water, and then dried to obtain 4.22 g (yield: 48%) of 5-(p-methoxyphenyl)-3-methyl-hydantoin.

EXAMPLE 12

4.0 g (40 mmol) of hydantoin, 30 ml of acetic acid and 2.0 ml (40 mmol) of bromine were mixed at room temperature. The reaction mixture was then vigorously stirred at a temperature of 60° C. for 2 hours. After cooling the reaction mixture to room temperature, 8.64 g (80 mmol) of anisol was added to the reaction mixture and the reaction was further conducted at a temperature of 100° C. for 6 hours. The resulting precipitate was recovered by filtration, washed with water, and then dried to obtain 3.96 g (yield 48%) of 5-(p-methoxyphenyl)hydantoin.

EXAMPLE 13

4.0 g (40 mmol) of hydantoin, 10 ml of dioxane, 0.01 g of methanesulfonic acid, and 2.0 ml (40 mmol) of bromine were mixed at room temperature. The reaction mixture was then vigorously stirred at a temperature of 120° C. for 5 minutes. The reaction mixture was then allowed to cool to room temperature. To the reaction mixture was then added 12.37 g (60 mmol) of 2,5-t-butylphenol. The reaction mixture was then allowed to undergo reaction at a temperature of 25 ° C. for 8 hours. The resulting precipitate was recovered by filtration, washed with water, and then dried to obtain 7.42 g (yield: 61%) of 5-(p-hydroxy-2,5-t-butylphenyl)-hydantoin.

EXAMPLE 14

4.0 g (40 retool) of hydantoin, 30 ml of acetic acid and 2.0 ml (40 mmol) of bromine were mixed at room temperature. The reaction mixture was then vigorously stirred at a temperature of 60° C. for 2 hours. After cooling the reaction mixture to room temperature, 11.0 g (60 mmol) of phenyl benzyl ether was added to the reaction mixture and the reaction was further conducted at a temperature of 40° C. for 12 hours. The resulting precipitate was recovered by filtration, washed with water, and then dried to obtain 5.4 g (yield 48%) of 5-(P-benzyloxyphenyl) hydantoin.

The foregoing examples are related to the deprotection and the optical resolution to an arylglycine.

EXAMPLE 15

10.3 g (50 mmol) of 5-(p-methoxyphenyl)hydantoin obtained in the same manner as in Example 12 was treated in a mixture (1:1) of acetic acid and a 48% HBr aqueous solution under reflux for 1 hour. After removing the solvent under reduced pressure, the residue was recrystallized from water to obtain 6.0 g (yield: 62% ) of 5-(p-hydroxyphenyl) hydantoin. Synthesis of p-hydroxyphenylglycine from 5-(p-hydroxyphenyl) hydantoin and optical resolution thereof to (D)-p-hydroxyphenylglycine

EXAMPLE 16

(Synthesis of p-hydroxyphenylglycine)

19.2 g (100 mmol) of 5-(p-hydroxyphenyl)hydantoin was heated under reflux in 200 ml of a 20% (w/w) aqueous solution of sodium hydroxide for 24 hours. The reaction solution was then allowed to cool to room temperature. The reaction solution was then adjusted with concentrated hydrochloric acid to pH 4. The resulting product was recovered by filtration, and then washed with 10 ml of water and with 10 ml of acetone three times. The resulting white solid matter was then dried under reduced pressure to obtain 8.68 g (52%) of p-hydroxyphenylglycine in the form of crude crystal. The infrared spectrum and NMR spectrum of the crude crystal coincided with that of a standard specimen of p-hydroxyphenylglycine.

EXAMPLE 17

(Optical resolution of p-hydroxyphenylglycine)

3.0 g of p-hydroxyphenylglycine and 5.9 g of d-bromocamphorsulfonic acid were dissolved in 30 ml of boiling water. The reaction solution was then stirred at room temperature for 2 hours. The resulting crystal was recovered by filtration, washed with water, and then dried to obtain 4.0 g of (D)-p-hydroxyphenylglycine d-bromocamphorsulfonate in the form of crude crystal. The crude crystal was then recrystallized from 3 ml of d-bromocamphorsulfonic acid to obtain 3.5 g of (D)-p-hydroxyphenylglycine d-bromocamphorsulfonate which was determined to be optically pure by the comparison of specific rotation with the standard specimen. $[\alpha]^{25}_D$–2.8°(c=1; 1N—HCl)

3.0 g of the pure (D)-p-hydroxyphenylglycine d-bromocamphorsulfonate was dissolved in 25 ml of boiling water. The reaction solution was then adjusted with an aqueous solution of sodium hydroxide to pH 6. The reaction solution was then concentrated to make 7 g. The reaction solution was then stirred at a temperature of 5° C. for 2 hours. The resulting precipitate was recovered by filtration, washed with water, and then dried to obtain 0.9 g of (D)-p-(hydroxyphenyl) glycine. $[\alpha]^{25}_D$–158.1°(c=1; 1N—HCl)

EXAMPLE 18

(Deprotection of benzyl group after optical resolution)

5-(p-benzyloxyphenyl)hydantoin was subjected to hydrolysis in a conc. NaOH aqueous solution, followed by optical resolution in a conventional manner, whereby (D)-p-benzyloxyphenylglycine.

5.1 g (20 mmol) of (D)-p-benzyloxyphenylglycine, 200 mg of 5% Pd-C and 30 ml of acetic acid were charged in an osmosis type medium-pressure hydrogen reducing apparatus to which hydrogen was introduced at 80° C. for 3 hours. Thereafter, the Pd-C was removed by filtration and the acetic acid was distilled off, whereby 3.1 g (yield: 92%) of (D)-p-hydroxyphenylglycine was obtained. $[\alpha]^{23}_D$–157.9°(c=1; 1N—HCl)

The following examples are related to the synthesis of a β-lactam antibiotic.

An example of the synthesis of a dane salt will be described below.

EXAMPLE 19

(Synthesis of potassium N-(1-alkoxycarbonylpropene-2-il)-(D)-α-amino-(p-hydroxyphenyl)acetate)

Into a 200-ml flask were charged 5.82 g (98.5 mmol; purity: 95%) of potassium hydroxide and 95 ml of methanol at room temperature to make a solution. To the reaction solution was then added 16.72 g (100 mmol) of (D)-p-hydroxy-phenylglycine. The reaction mixture was then stirred at room temperature for 1 hour. To the reaction mixture was then added 12.19 g (105 mmol) of methyl acetoacetate at once. The reaction mixture was then heated under reflux for 2 hours. The reaction solution was then cooled to a temperature of 10° C. The resulting crystal was recovered by filtration, and then washed with 10 ml of methanol three times. The resulting crude crystal was then dried under reduced pressure to obtain 26.0 g (yield: 86%) of potassium N-(1-alkoxy-carbonylpropene-2-il)-(D)-α-amino-(p-hydroxyphenyl) acetate.

An example of the synthesis of an antibiotic will be described below.

EXAMPLE 20

(Synthesis of amoxicillin)

Into a 50-ml eggplant type flask were charged 7 ml of acetone and 1.23 g (4.05 mmol) of potassium N-(1-alkoxycarbonylpropene-2-il)-(D)-α-amino-(p-hydroxyphenyl) acetate thus obtained. The reaction mixture was then cooled to a temperature of −10° C. To the reaction mixture were then added 0.50 g (4.50 mmol; purity: 97%) of ethyl chloroformate and 10 mg of N-methylmorpholine. The reaction mixture was then stirred for 15 minutes. The reaction mixture was then added to a solution obtained by dissolving 0.82 g (3.8 mmol) of 6-aminopenicillanic acid which had been previously prepared in a mixture of 4 ml of a 5% potassium hydroxide solution and 3 ml of acetone. The reaction mixture was then stirred at room temperature for 2 hours. The reaction solution was then adjusted with an aqueous solution of hydrochloric acid to pH 2 while being cooled with ice. To the reaction solution was then added 15 ml of cooled methylene chloride. The reaction mixture was then stirred for 5 minutes. The resulting aqueous phase was then separated. The residual organic phase was then subjected to distillation under reduced pressure in an evaporator over a 10° C. water bath. The residue was then adjusted with an aqueous solution of sodium hydroxide to pH 5. The residue was then stirred at a temperature of 5° C. for 3 hours. The resulting crystal was recovered by filtration, and then washed with 2 ml of water and 1 ml of acetone to obtain 1.0 g (yield: 63%) of amoxicillin trihydrate. $[\alpha]^{23}_D$+293°(c0.2; $H_2O$)

In accordance with the present invention, a high purity 5-arylhydantoin can be obtained by reacting a hydantoin which is unsubstituted at the 5-position with a halogenating agent, and then reacting the product with a phenol compound wherein the hydroxyl group at its para position may be protected. In other words, the present invention provides a process for the preparation of an intermediate material extremely useful for the preparation of (D)-arylglycines, which are important intermediate for the synthesis of semi-synthetic penicillin antibiotics.

While the invention has been described in detail and with reference to specific embodiments thereof, it will be apparent to one skilled in the art that various changes and modifications can be made therein without departing from the spirit and scope thereof.

What is claimed is:

1. A process for producing a 5-arylhydantoin which comprises (i) reacting a 5-unsubstituted hydantoin compound with a halogenating agent and (ii) reacting the resulting product with a p-unsubstituted phenol compound, the hydroxy group of which is protected, or unprotected to substitute the 5-position of the hydantoin compound with the phenol compound at the para position.

2. The process as in claim 1, wherein said p-unsubstituted phenol compound is represented by formula (III)

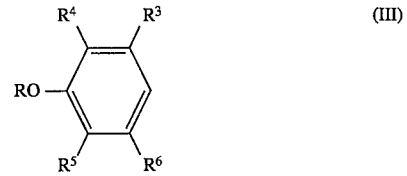

wherein R represents a hydrogen atom or a protective group for phenolic hydroxy group and $R^3$, $R^4$, $R^5$ and $R^6$ each represent a hydrogen atom or a group which does not substantially impair the para-orientation property of phenol compound.

3. A process as in claim 1, wherein said 5-unsubstituted hydantoin compound is represented by formula (I)

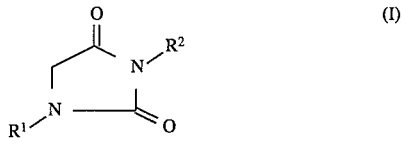

wherein $R^1$ represents a hydrogen atom or a protective group for nitrogen atom, and $R^2$ represents a hydrogen atom, and alkyl group having 1 to 8 carbon atoms, an alkenyl group having 3 to 10 carbon atoms, an alkynyl group having 3 to 10 carbon atoms, an acyl group having 2 to 10 carbon atoms, an aryl group, an aralkyl group, an aminocarbonyl group which may have a substituent on the amino moiety, an alkoxycarbonyl group having 2 to 8 carbon atoms, an aryloxycarbonyl group, an aralkyloxycarbonyl group a sulfinyl group having 1 to 8 carbon atoms, a sulfonyl group having 1 to 8 carbon atoms, or an azo group.

4. The process as in claim 1, wherein said p-unsubstituted phenol compound and said 5-unsubstituted hydantoin compound are phenol and hydantoin, respectively, and said 5-arylhydantoin is 5-(p-hydroxyphenyl) hydantoin.

5. The process as in claim 1, wherein said reaction (i) is conducted in the presence of an acid.

6. The process as in claim 1, wherein said reaction (i) is conducted in the presence of a radical reaction initiator.

7. The process as in claim 1, wherein said reaction (i) is conducted in a solvent containing substantially no water.

8. A process for producing a of 5-arylhydantoin represented by formula (IV)

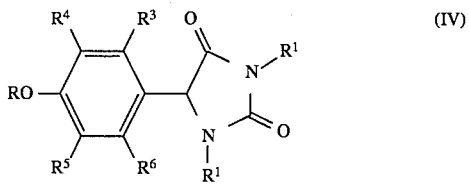

wherein R represents a hydrogen atom or a protective group for phenolic hydroxy group; $R^1$ represents a hydrogen atom or a protective group for nitrogen atom, and $R^2$ represents a hydrogen atom, and alkyl group having 1 to 8 carbon atoms, an alkenyl group having 3 to 10 carbon atoms, an alkynyl group having 3 to 10 carbon atoms, an acyl group having 2 to 10 carbon atoms, an aryl group, an aralkyl group an aminocarbonyl group, an alkoxycarbonyl group having 2 to 8 carbon atoms, an aryloxycarbonyl group, an aralkyloxycarbonyl group, a sulfinyl group having 1 to 8 carbon atoms, a sulfonyl group having 1 to 8 carbon atoms, or an azo group; and $R^3$, $R^4$, $R^5$ and $R^6$ each represent a hydrogen atom or a group which does not substantially impair the para-orientation property of phenol compound, which comprises the reaction of a 5-halo-hydantoin compound represented by formula (II') and a p-unsubstituted phenol compound represented by formula (III):

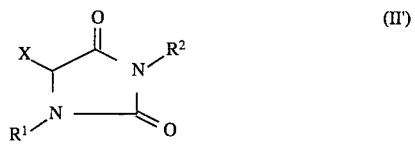

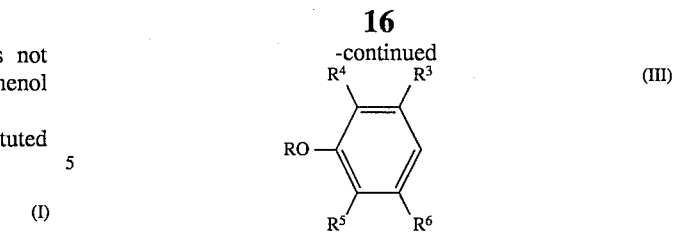

wherein X represents a chlorine atom, a bromine atom, or an iodine atom.

9. The process as in claim 8, wherein said p-unsubstituted phenol compound and said 5-unsubstituted hydantoin compound are phenol and hydantoin, respectively, and said 5-arylhydantoin is 5-(p-hydroxyphenyl)hydantoin.

10. The process as in claim 8, wherein said reaction (i) is conducted in a solvent containing substantially no water.

11. The process as in claim 1, wherein the p-unsubstituted phenol compound comprises a hydroxy group.

12. The process as in claim 1, wherein the p-unsubstituted phenol compound comprises a hydroxy group and a hydroxy protective group selected from the group consisting of an alkyl group having 1 to 8 carbon atoms, an alkenyl group having 3 to 10 carbon atoms, an alkynyl group having 3 to 10 carbon atoms, an acyl group having 2 to 10 carbon atoms, an aralkyl group, an aminocarbonyl group, an alkoxycarbonyl group having 3 to 8 carbon atoms, an aryloxycarbonyl group, an aralkyloxycarbonyl group, a trialkylsilyl group having an alkyl moiety with 1 to 4 carbon atoms, a dialkylarylsilyl group having an alkyl moiety with 1 to 4 carbon atoms, an alkyldiarylsilyl group having an alkyl moiety with 1 to 4 carbon atoms, a triarylsilyl group, and a phosphate ester derivative.

13. The process as in claim 2, wherein the protective group for the phenolic hydroxy group is the protective group selected from the group consisting of an alkyl group having 1 to 8 carbon atoms, an alkenyl group having 3 to 10 carbon atoms, an alkynyl group having 3 to 10 carbon atoms, an acyl group having 2 to 10 carbon atoms, an aralkyl group, an aminocarbonyl group, an alkoxycarbonyl group having 3 to 8 carbon atoms, an aryloxycarbonyl group, an aralkyloxycarbonyl group, a trialkylsilyl group having an alkyl moiety with 1 to 4 carbon atoms, a dialkylarylsilyl group having an alkyl moiety with 1 to 4 carbon atoms, an alkyldiarylsilyl group having an alkyl moiety with 1 to 4 carbon atoms, a triarylsilyl group, and a phosphate ester derivative.

14. The process as in claim 3, wherein the protective group for the nitrogen atom is selected from the group consisting of a methyl group, an alkenyl group having 3 to 10 carbon atoms, an alkynyl group having 3 to 10 carbon atoms, an acyl group having 2 to 10 carbon atoms, an aralkyl group, an aminocarbonyl group, an alkoxycarbonyl group having 3 to 8 carbon atoms, an aryloxycarbonyl group, and an aralkyloxycarbonyl group.

15. The process as in claim 8, wherein the protective group for the phenolic hydroxy group representing R is selected from the group consisting of an alkyl group having 1 to 8 carbon atoms, an alkenyl group having 3 to 10 carbon atoms, an alkynyl group having 3 to 10 carbon atoms, an acyl group having 2 to 10 carbon atoms, an aralkyl group, an aminocarbonyl group, an alkoxycarbonyl group having 3 to 8 carbon atoms, an aryloxycarbonyl group, an aralkyloxycarbonyl group, a trialkylsilyl group having an alkyl moiety with 1 to 4 carbon atoms, a dialkylarylsilyl group having an alkyl moiety with 1 to 4 carbon atoms, an alkyldiarylsilyl group having an alkyl moiety with 1 to 4 carbon atoms, a triarylsilyl group, and a phosphate ester derivative, and wherein the protective group for the nitrogen atom representing $R^1$ is selected from the group consisting of a methyl group, an alkenyl group having 3 to 10 carbon atoms, an alkynyl group having 3 to 10 carbon atoms, an acyl group having 2 to 10 carbon atoms, an aralkyl group, an aminocarbonyl group, an alkoxycarbonyl group having 3 to 8 carbon atoms, an aryloxycarbonyl group, and an aralkyloxycarbonyl group.

16. The process as in claim 3, wherein the aryl group, the aralkyl group, the aminocarbonyl group, the aryloxycarbonyl group and the aralkyloxycarbonyl group representing $R^2$ are unsubstituted.

17. The process as in claim 3, wherein the aryl group, the aryl moiety on the aralkyl group, the amino moiety on the aminocarbonyl group, the aryl moiety on the aryloxycarbonyl group, and the aryl moiety on the aralkyloxycarbonyl group representing $R^2$ are substituted with a methyl group or a methoxy group.

18. The process as in claim 8, wherein the aryl group, the aralkyl group, the aminocarbonyl group, the aryloxycarbonyl group and the aralkyloxycarbonyl group representing $R^2$ are unsubstituted.

19. The process as in claim 8, wherein the aryl group, the aryl moiety on the aralkyl group, the amino moiety on the aminocarbonyl group, the aryl moiety on the aryloxycarbonyl group, and the aryl moiety on the aralkyloxycarbonyl group representing $R^2$ are substituted with a methyl group or a methoxy group.

20. The process as in claim 2, wherein the group which does not substantially impair the para-orientation property of the phenol compound is selected from the group consisting of a halogen atom, a hydroxy group, an alkyl group having 1 to 4 carbon atoms, an alkoxy group having 1 to 4 carbon atoms, an alkoxy carbonyl group having 1 to 4 carbon atoms, an amino group, an aminocarbonyl group having 1 to 10 carbon atoms, a nitoro group, a nitroso group, a thiol group and a sulfide group having 1 to 4 carbon atoms.

21. The process as in claim 8, wherein the group which does not substantially impair the para-orientation property of the phenol compound is selected from the group consisting of a halogen atom, a hydroxy group, an alkyl group having 1 to 4 carbon atoms, an alkoxy group having 1 to 4 carbon atoms, an alkoxy carbonyl group having 1 to 4 carbon atoms, an amino group, an aminocarbonyl group having 1 to 10 carbon atoms, a nitoro group, a nitroso group, a thiol group or a sulfide group having 1 to 4 carbon atoms.

* * * * *